United States Patent [19]

Shah et al.

[11] Patent Number: 4,532,414
[45] Date of Patent: Jul. 30, 1985

[54] CONTROLLED TEMPERATURE BLOOD WARMING APPARATUS

[75] Inventors: Ramesh M. Shah, Indianapolis, Ind.; Thomas H. Ridgway, Cincinnati, Ohio

[73] Assignee: Data Chem., Inc., Indianapolis, Ind.

[21] Appl. No.: 260,035

[22] Filed: May 4, 1981

Related U.S. Application Data

[63] Continuation-in-part of Ser. No. 148,731, May 12, 1980, abandoned.

[51] Int. Cl.$^3$ .................. H05B 1/02; B67D 5/62; A61F 7/00; F24H 1/12
[52] U.S. Cl. .................................. 219/308; 128/399; 165/46; 219/299; 219/302; 219/305; 219/328; 219/330; 219/497; 219/499; 219/501; 219/524; 219/535; 222/146.5; 604/114
[58] Field of Search ........ 219/296, 298, 299, 301–305, 219/280, 308, 309, 328, 330, 535, 524, 525, 497–499, 501; 604/114; 128/399, 401; 222/146 HE; 165/46

[56] References Cited

U.S. PATENT DOCUMENTS

| | | | |
|---|---|---|---|
| 2,102,523 | 12/1937 | Ferrara et al. | 219/302 X |
| 2,357,238 | 8/1944 | Trimble | 128/395 |
| 2,470,481 | 5/1949 | Freeman | 128/214 A |
| 2,523,182 | 8/1950 | Phillips et al. | 219/501 |
| 2,947,915 | 8/1960 | Patchell | 219/501 X |
| 3,107,285 | 10/1963 | Knapp | 219/499 X |
| 3,140,716 | 7/1964 | Aarrison et al. | 128/399 |
| 3,154,663 | 10/1964 | Halvorsen | 219/10.49 |
| 3,247,851 | 4/1966 | Seibert | 128/254 |
| 3,275,802 | 9/1966 | Vandivere | 219/499 |
| 3,293,868 | 12/1966 | Gonzalez | 219/302 X |
| 3,315,681 | 4/1967 | Popendiek | 128/399 |
| 3,370,153 | 2/1968 | Du Fresne et al. | 219/302 |
| 3,443,060 | 5/1969 | Smith | 219/302 |
| 3,475,590 | 10/1969 | Pins | 219/302 |
| 3,480,015 | 11/1969 | Gonzalez | 604/114 |
| 3,485,245 | 12/1969 | Lahr et al. | 604/114 |
| 3,551,641 | 12/1970 | Truhan | 219/303 |
| 3,553,429 | 1/1971 | Nelson | 219/499 X |
| 3,590,215 | 6/1971 | Anderson et al. | 128/214 A X |
| 3,614,385 | 10/1971 | Horstman | 219/303 |
| 3,624,355 | 11/1971 | Friedrichs | 219/497 |
| 3,629,552 | 12/1971 | Edging | 219/302 |
| 3,908,652 | 9/1975 | Weissinger | 128/214 A X |
| 4,019,020 | 4/1977 | Bilbee et al. | 219/302 |
| 4,089,207 | 5/1978 | Patton | 219/535 |
| 4,091,266 | 5/1978 | Ito et al. | 219/501 X |
| 4,167,663 | 9/1979 | Granzow et al. | 219/497 |
| 4,293,762 | 10/1981 | Ogawa | 219/308 |
| 4,314,143 | 2/1982 | Bilstad et al. | 604/114 X |
| 4,356,383 | 10/1982 | Dahlberg et al. | 219/308 |
| 4,358,664 | 11/1982 | Kronseder | 219/308 |

FOREIGN PATENT DOCUMENTS

| | | | |
|---|---|---|---|
| 2514376 | 10/1976 | Fed. Rep. of Germany | 219/302 |
| 2619438 | 11/1977 | Fed. Rep. of Germany | 219/302 |
| 2331230 | 6/1977 | France | 219/302 |
| 1446412 | 8/1976 | United Kingdom | 219/302 |
| 1578015 | 10/1980 | United Kingdom | 219/302 |

Primary Examiner—A. Bartis
Attorney, Agent, or Firm—Frost & Jacobs

[57] ABSTRACT

An in-line fluid warmer for heating parenteral fluids, particularly blood, supplied from a fluid container through a flexible supply conduit. The fluid warmer includes a box-like enclosure containing a heated plate having a sinuously-shaped groove configured to accept and hold a length of the supply conduit in heat transfer relationship with the plate. A pair of temperature sensors monitor the actual temperature of the plate. One of the temperature sensors controls a voltage controlled oscillator, while the other is used to determine maximum permissible plate temperature. The voltage controlled oscillator supplies proportional control to the heated plate up to a predetermined temperature of 37° C. for warming blood. In the event that the temperature of the plate exceeds the predetermined temperature, or in the event that component failure occurs, or in the event the maximum permissible temperature of the plate is exceeded, oscillation from the voltage controlled oscillator ceases, and the heater is de-energized. Consequently, the parenteral fluid such as blood is protected from overheating.

6 Claims, 9 Drawing Figures

CONTROLLED TEMPERATURE BLOOD WARMING APPARATUS

SUMMARY OF THE INVENTION

This application is a continuation in part of U.S. patent application Ser. No. 06/148,731, filed May 12, 1980 by the present inventor for "Controlled Temperature Blood Warming Apparatus", now abandoned.

This invention is directed generally to fluid warming devices, and more particularly to a device for warming cold parenteral fluids such as whole blood under controlled temperature conditions for transfusion procedures and the like.

Generally, whole donor blood is maintained under refrigerated conditions at temperatures of approximately 4° C. to preserve the quality of the blood over extended periods of time. However, when the blood is infused into a patient, it is necessary that the blood be warmed to approximate body temperature to avoid hypothermia and the attendant risk of ventricular fibrillation and cardiac asystole. On the other hand, if the blood temperature is permitted to rise excessively, the blood may coagulate or deteriorate.

For many surgical procedures, a sufficient quantity of blood must be warmed to meet unexpected emergencies that may arise such as where a patient hemorrhages during surgery. In many instances, all of the blood is not used, resulting in waste of the excess whole blood, since it cannot be again refrigerated. For accident victims or other emergency cases, the time required to warm blood for transfusion is often a critical factor. Consequently, in emergency room situations, it is essential to maintain sufficient effective blood heating capacity to quickly raise the temperature of the refrigerated whole blood to the approximate temperature of the human body for infusion.

Many approaches have been suggested for meeting the need of effective and reliable apparatus for quickly warming parenteral fluids such as whole blood to approximate body temperature. For example, one type of device utilizes a permanently mounted heated plastic or metal tube through which the whole blood flows from a blood container to the patient. Similarly, the tubing may be replaced by a canister or container which provides the proper residence time for the blood to insure heating to the proper temperature. Both types of devices, however, must be thoroughly cleaned after each use, and cannot readily be converted to supply warmed blood of a different type, for example. Furthermore, the unit must be thoroughly sterilized before use to insure that the blood is not contaminated by foreign material within the warming unit. It has also been suggested to use disposable plastic pouches or bags containing whole blood which may be warmed by contact with electrically heated plates to warm the fluid contained within the bag. Such devices, however, generally require considerable periods of time to insure uniform heating of the fluid, while also requiring considerable time and skill in assembling and using the apparatus.

U.S. Pat. No. 3,293,868 issued Dec. 27, 1966 to F. A. Gonzalez for "Fluid Cooling Apparatus" describes a device having a flat plate with sinuous-shaped upstanding fins which form a channel for holding a length of flexible tubing through which blood or the like may be passed for heating or cooling. The plate is in contact with a number of spaced thermocouples which operate by virtue of the Peltier effect to heat or cool the plate depending upon the direction current is passed through the thermocouples. A rotary blower may be further utilized to remove heat from the fluid. The device is designed to be used in a generally horizontal position with the blood or other fluid being forced through the tubing by a pump or the like. The apparatus also lacks means for monitoring and displaying the actual temperature of the blood.

The blood warmer of the present invention seeks to overcome the disadvantages of prior art blood warming devices by providing apparatus which effectively and quickly warms the whole blood to the proper body temperature, and requires minimal training for proper operation. The fluid warmer operates in-line by serving to warm the fluid flowing through the flexible supply conduit attached between the fluid container and the intravenous needle or the like. In a preferred embodiment, the fluid warmer comprises a box-like fluid warmer enclosure having a closable hinged lid and latch means for securing the lid in a closed position. A generally rectangular substantially planar heat conducting heating plate is positioned within the enclosure, with the upper surface of the plate including a sinuously-shaped groove configured to accept and hold a length of the supply conduit in heat transfer relationship with the plate. With the lid of the fluid warmer open, the supply conduit is inserted into the groove, with the conduit entering the enclosure at an upper corner, and exiting at the opposite lower corner. This arrangement permits the fluid warmer to be suspended beneath the fluid supply container on the same support pole so that the blood or other parenteral fluid will flow by gravity from the supply container to the patient without the need for special pumps and the like.

A resilient pad is secured to the underside of the lid and serves to press the supply conduit against the upper surface of the heating plate when the lid is in the closed position to insure good heat transfer. A thin flexible electrically operated heating pad is attached to the lower surface of the plate for heating the plate to a predetermined temperature which overcomes the problem of "spot heating" encountered with some blood warming devices. A first temperature sensing element provides an electrical signal representative of the temperature of the plate. Circuit means responsive to this electrical signal control the heating element to maintain the temperature of the plate at approximately 37° C. A liquid crystal display also responsive to this electrical signal provides a visual indication of the temperature of the plate. A second temperature sensing element provides a second electrical signal representative of the temperature of the plate which is compared to a predetermined reference voltage representative of the maximum safe operating temperature for the heating plate. When the temperature of the plate exceeds this value, an audible alarm is actuated, and the heating element is de-energized to prevent overheating of the fluid. The electrical control means also include electronic circuitry for insuring fail-safe operation of the heating element in the event of component failure. The status of primary power and heating element operation are monitored by visual indicators positioned on the external causing of the unit.

In another embodiment, the sinuous-shaped groove is provided with non-parallel straight sections which permit more tubing to be placed in contact with the heated surface of the heating plate, so that the blood may be warmed more quickly. Furthermore, an additional upper plate may be provided also containing a sinuous-shaped groove which is heated under control of the electronic circuitry to heat both the upper and lower semi-cylindrical surfaces of the flexible tubing.

Further features of the invention will become apparent from the detailed description which follows.

DETAILED DESCRIPTION

Figures 1, 2:
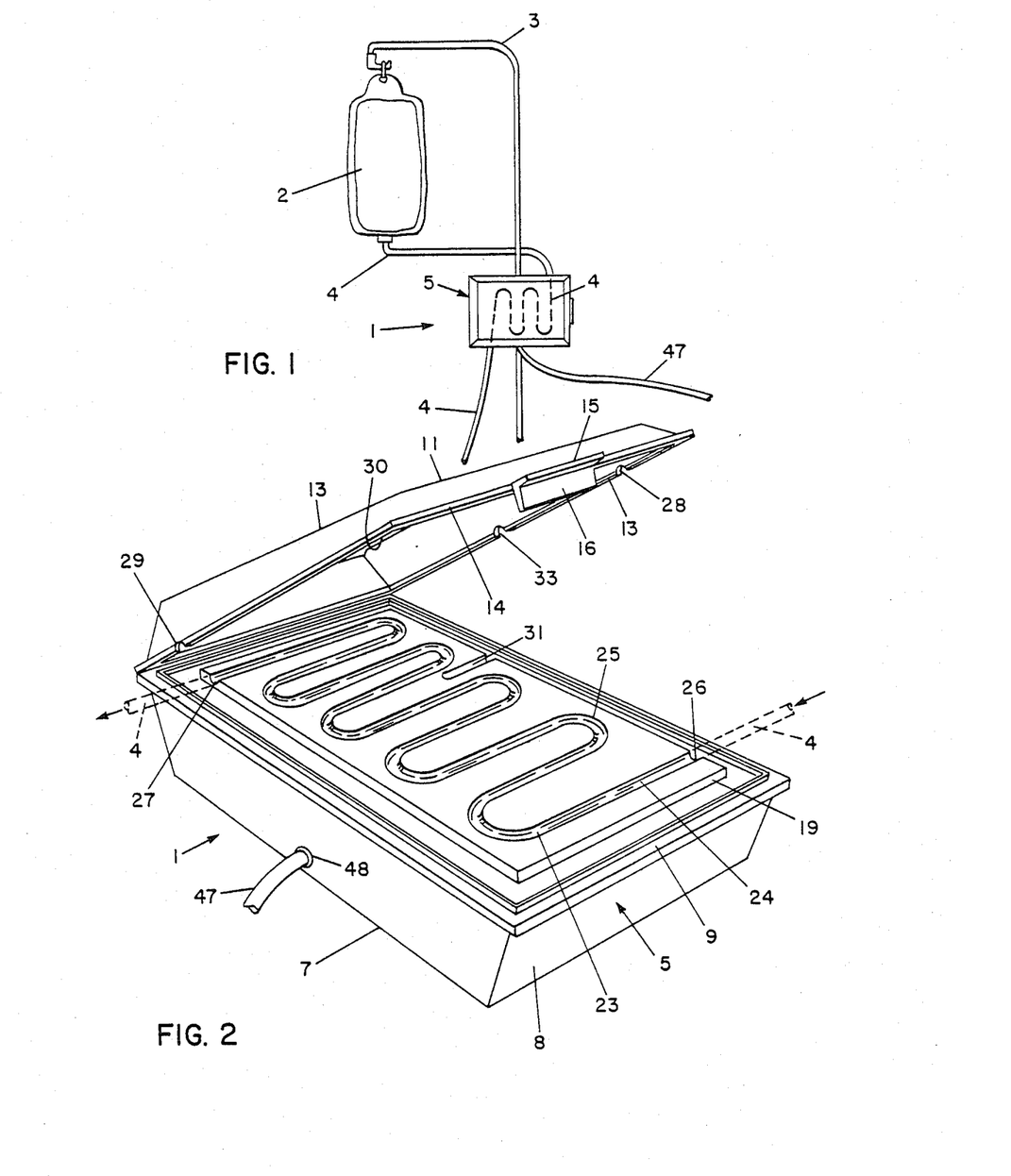
FIG. 1 is a fragmentary elevation view of the fluid of the present invention in a typical operating environment.
FIG. 2 is a front perspective view of the fluid warmer of the present invention with the hinged cover in the raised position.

The fluid warmer, shown generally at 1, is illustrated in FIG. 1 in a typical operating environment. A bag-like receptacle 2 of an intravenous or parenteral fluid such as whole blood and the like is suspended from a suitable IV pole 3. A continuous flexible IV tube or supply conduit 4 connects container 2 with a suitable IV needle or the like (not shown). Fluid warmer 1 is secured to IV pole 3 and encloses a length of supply conduit 4, thereby serving to warm the fluid as it passes through the supply conduit. It will be observed that this construction permits fluid warmer 1 to be located in close proximity to the patient, and eliminates the need to interrupt the continuous supply conduit with connections, fittings and the like as in prior art fluid warmer designs. Furthermore, the fluid may flow by gravity from supply receptacle 2 without the need for pumps and the like.

Fluid warmer 1 comprises a box-like fluid warmer enclosure 5 having a rectangular substantially planar bottom portion 6 supporting upwardly and outwardly extending side walls 7 and end walls 8. Enclosure 5 may be constructed of any suitable material such as unbreakable plastic or the like, and may be cast or molded in a single piece.

The upper edges of side walls 7 and end walls 8 are provided with an outwardly extending lip 9 and an inwardly extending ledge or shelf 10. The forwardmost lip 9 (see FIG. 2) cooperates with latching means to hold the hinged cover in the closed position, while the inwardly extending ledge 10 serves to support the heating plates as will be described in more detail hereinafter.

Enclosure 5 is also provided with a cover or lid 11 hingedly secured to the upper edge of rear end wall 8 adjacent lip 9 by means of a continuous flexible hinge extending the width of enclosure 5. In the preferred embodiment illustrated, hinge 12 comprises a thin web-like section formed as an integral part of enclosure 5 and cover 11 to provide a flexible means of attachment between these members. As a result, the enclosure and cover may be formed at the same time in one continuous molding operation. Alternatively, hinge 12 may be formed as a separate part, and secured by any convenient means to the cover and enclosure body. It will be further understood that hinge 12 may be dispensed with entirely, and cover 11 removably secured to enclosure body 5 by any convenient attaching means such as clamps, snaps, or the like.

Figure 4:
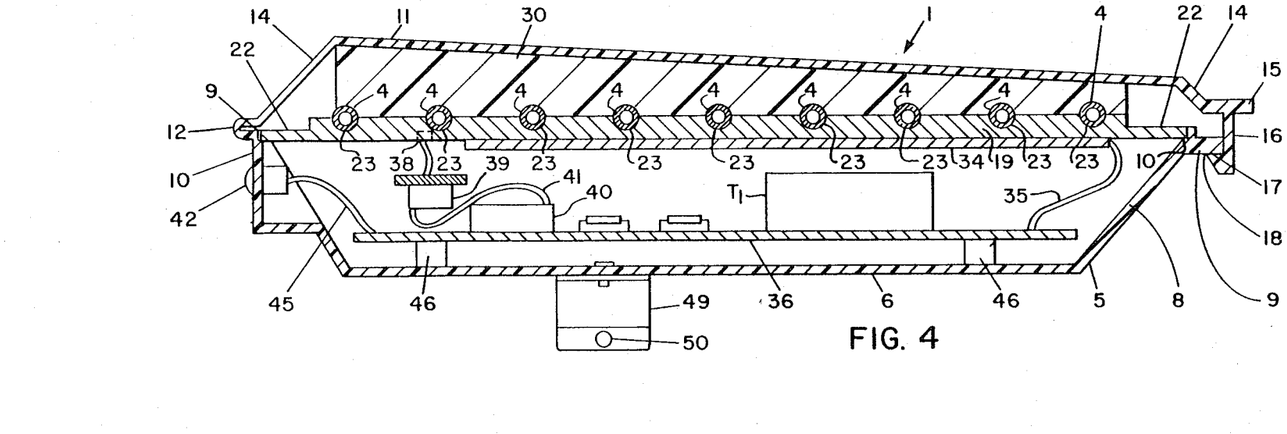
FIG. 4 is a cross sectional view of the fluid warmer of the present invention taken along the longitudinal centerline of the warmer with the hinged cover in the closed position.
Figure 5:
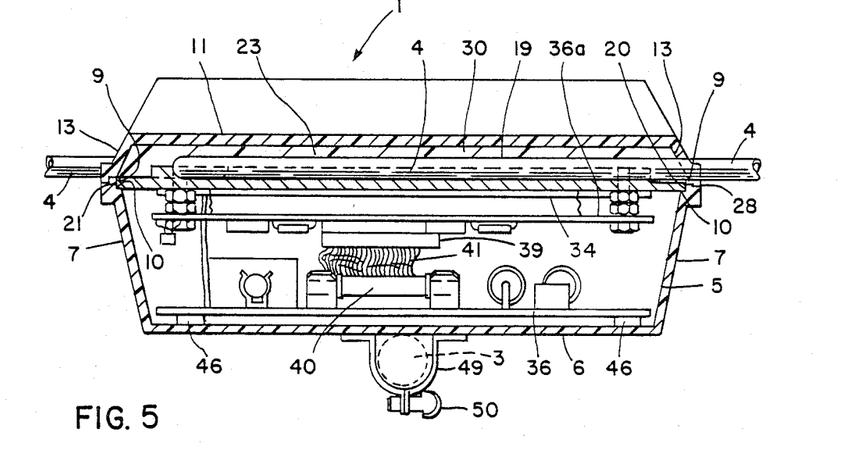
FIG. 5 is a cross sectional view of the fluid warmer of the present invention taken along the transverse centerline of the warmer with the hinged cover in the closed position.

Cover 11 comprises a generally shallow box-like construction having perpendicularly arranged downwardly and outwardly extending side and end wall portions, 13 and 14, respectively. The lower edges of the cover side and end walls are configured to smoothly mate with the upper edges of the enclosure side and end walls to provide a tight-fitting enclosure unit when the cover is in the closed position as illustrated in FIG. 4 and FIG. 5.

As described hereinabove, the lowermost edge of the cover rear end wall 14 is hingedly secured to the uppermost edge of the rear enclosure end wall 8. Front cover end wall 14 is provided with an outwardly extending lip 15 configured to be grasped by the user's fingers to lift the cover 11 away from enclosure body 5. Handle 15 is provided with a downwardly depending web 16 which terminates in a rearwardly extending catch or projection 17. As best shown in FIG. 4, the rear edge of catch 17 is beveled as at 18 so as to slide downwardly past the forward edge of the adjacent lip 9, thereby biasing downwardly depending web 16 forwardly as the cover 11 is closed. When the upper edge of catch 17 is positioned beneath the lower edge surface of the adjacent lip 9, web 16 will return to the position illustrated in FIG. 4 abutting the front edge of lip 9, and thereby serving as effective latching means to hold the cover 11 in the closed position. When it is desired to raise the cover, web 16 may be biased forwardly such that catch 17 clears the forward edge of the adjacent lip 9, thereby releasing the latching means. It will be understood, however, that other types of latch means may be used as required to secure the cover in a closed position.

A rectangular substantially planar heating plate 19 is secured within enclosure 5 in spaced parallel relationship with enclosure bottom portion 6. Plate 19 may be constructed of any suitable heat conducting material such as anodized aluminum or the like. The side peripheral edges 20 and 21, as well as the end edges 22 of plate 19 are supported by the adjacent ledges 10 extending inwardly from the upper peripheral edges of the enclosure side and end walls. In general, enclosure 5 will be constructed of a non-heat conducting material to prevent heat transfer between plate 19 and the supporting structure.

Figure 3:
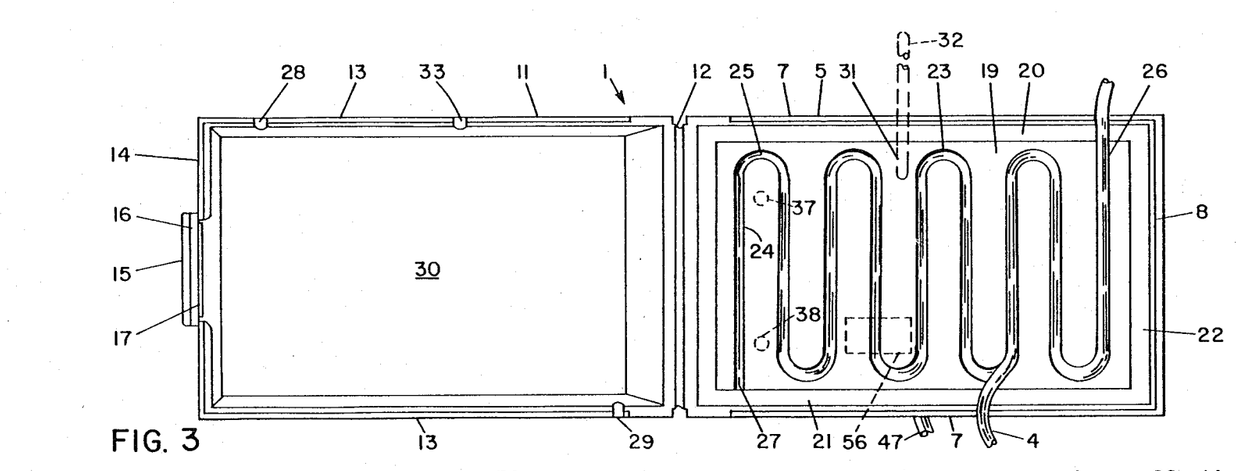
FIG. 3 is a top plan view of the fluid warmer of the present invention with the hinged cover opened and the flexible supply conduit being placed in position.

The upper surface of plate 19 is provided with a continuous sinuously-shaped groove 23 originating at the upper right corner of plate 19 adjacent side edge 20, and terminating at the opposite lower left hand corner of plate 19 adjacent side edge 21 (see FIG. 3). As best shown in FIG. 4, groove 23 will be dimensioned to accept and hole a length of supply conduit 4 in heat transfer relationship with the upper surface of plate 9. As shown in FIG. 3, groove 23 includes nine parallel straight portions, one of which is shown at 24, and eight arcuate portions 25 connecting straight portions 23. The radius of arcuate portions 25 is selected to minimize the possiblity of kinking of supply conduit 4. In addition, the total length of groove 23 is selected to provide the desired residence time of the fluid within the fluid warmer. In general, groove 23 will be of sufficient length to insure that the fluid is heated to approximate body temperature under normal flow conditions of approximately 8 ml. per minute, depending on the needs of the patient.

As shown in FIG. 3, the continuous supply conduit 4 is inserted in groove 23 beginning at entrance point 26, and pressed into groove 23 along its entire length, exiting at a point 27 located on the opposite corner of plate 19. Cover 11 is provided with notch portions 28 and 29 corresponding to entrance and exit points 26 and 27, respectively, to insure free passage of supply conduit 4 when cover 11 is closed.

To insure that supply conduit 4 is pressed into heat transfer engagement with the upper surface of heating plate 19, the underside of cover 11 is provided with a generally rectangular resilient pad 30 constructed of rubber, plastic or the like, which is slightly compressed against the upper surface of plate 19 when cover 11 is in the closed position as illustrated in FIG. 4, for example. It will be also understood, however, that resilient pad 30 may be eliminated by constructing cover 11 such that the underside presses directly against the upper surface of supply conduit 4 when the cover is closed. In any event, it will be understood that supply conduit 4 will be held in heat transfer engagement with plate 19 against displacement while preventing restriction of fluid flow through the conduit.

In some instances it may be desirable to visually monitor the actual temperature of heating plate 19. To provide for this contingency, heating plate 19 is supplied with a short centrally located groove-like channel 31 extending parallel to straight conduit groove portions 24 for accepting a suitable fever thermometer shown generally at 32 in FIG. 3. A suitable clearance hole or notch 33 may also be provided in cover 11 as required.

Heat is supplied to heating plate 19 by means of a thin sheet-like electrically operated heating pad 34 secured in heat transfer engagement with the underside of heating plate 19. For purposes of an exemplary showing, heating pad 34 may comprise a resistance heating element of the type formed by a plurality of Nichrome wires sandwiched between rubber or other resilient facing sheets. Electric current is supplied to heating pad 34 through electrical conductors 35 from electronic control circuitry to be described hereinabove located on circuit board 36 and circuit board 36a positioned in the lower portion of enclosure 5. Circuit board 36a has been omitted from FIG. 4 and FIG. 4A for clarity. It will be observed that this construction provides even heating of the flexible conduit surface in order to avoid hot spots which could overheat the fluid as could occur if a number of discrete spaced heating elements were utilized.

The temperature of heating plate 19 is monitored by means of temperature sensing elements 37 and 38 attached in heat transfer engagement with the underside of heating plate 19. Electrical connection may be made between temperature sensing elements 37 and 38, and circuit board 36 by means of suitable electrical connectors 39 and 40, and interconnecting cabling 41.

Figure 6:
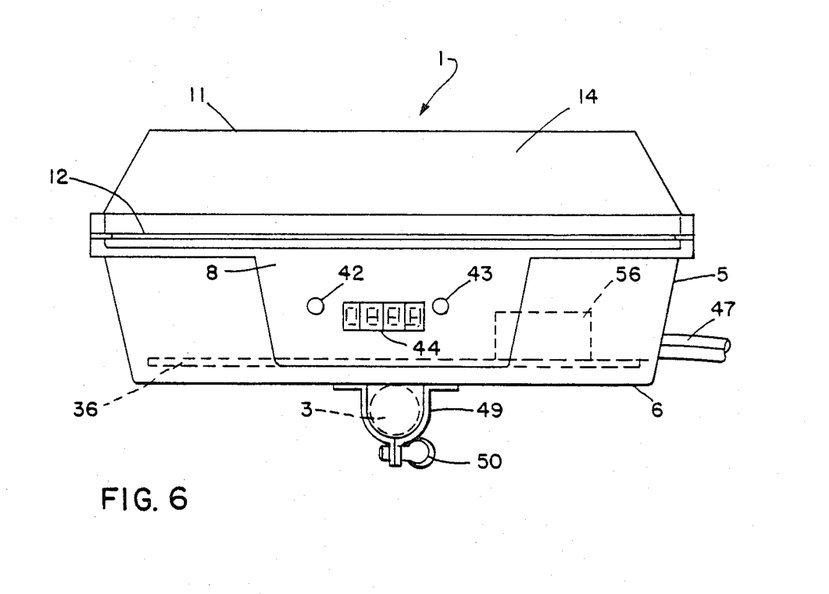
FIG. 6 is an end elevation view of the fluid warmer of the present invention with the hinged cover in the closed position.

In addition to thermometer 32, other visual indicator means may be provided such as those illustrated as mounted on rear end wall 8 of enclosure 5 (see FIG. 6). In particular, these visually sensible monitoring means comprise a pair of spaced light emitting diodes 42 and 43, and an intermediately positioned 3½ digit liquid crystal display 44. As will be explained in more detail hereinafter, LED 42 provides an indication that primary power is applied to fluid warmer 1, while LED 43, which may be of a distinguishing color, provides an indication that heating pad or element 34 is energized. Liquid crystal display 44 provides a direct digital readout of the actual temperature of heating plate 19, and may be calibrated to read in any suitable temperature units. Electrical connections between these display elements and the electronic control circuitry contained on circuit board 36 are made by means of suitable cabling illustrated generally at 45 in FIG. 4.

The electronic control circuitry of the fluid warmer of the present invention is located on planar printed circuit board 36 mounted in the lower portion of enclosure 5 by means of spaced stand-off mounting posts 46. Primary power is supplied to fluid warmer 1 by means of electrical conductor 47 passing through a cooperating aperture 48 in side wall 7 of enclosure 5. It will be understood that other well-recognized mounting configurations which insure easy assembly and servicing of the fluid warmer unit may also be utilized.

Means may also be provided for securing fluid warmer 1 to a suitable TV pole 3 or other support. In the present invention, the securing means comprise a generally circular or loop-like clamp 49 secured to the rear surface of fluid warmer 1, and having means in the form of a threaded screw 50, or the like, for tightly securing the clamp to a vertical post or pole 3. It will be understood, however, that other mounting arrangements may be used, and in fact the fluid warmer of the present invention may be mounted in any position as required. However, the unique locations of the entrance point 26 and exit point 27 for flexible conduit 4 on the upper and lower surfaces, respectively, when fluid warmer 1 is suspended vertically as shown in FIG. 1, permit the fluid to flow by gravity from the supply receptacle 2 to the patient without the need for pumps and the like. Furthermore, this construction permits the tubing to enter and exit the blood warmer housing from opposite sides, thereby preventing kinking or binding of the supply conduit. Neither of these features is to be found in prior art fluid warmers such as that illustrated in U.S. Pat. No. 3,293,868, for example.

Figure 3A:
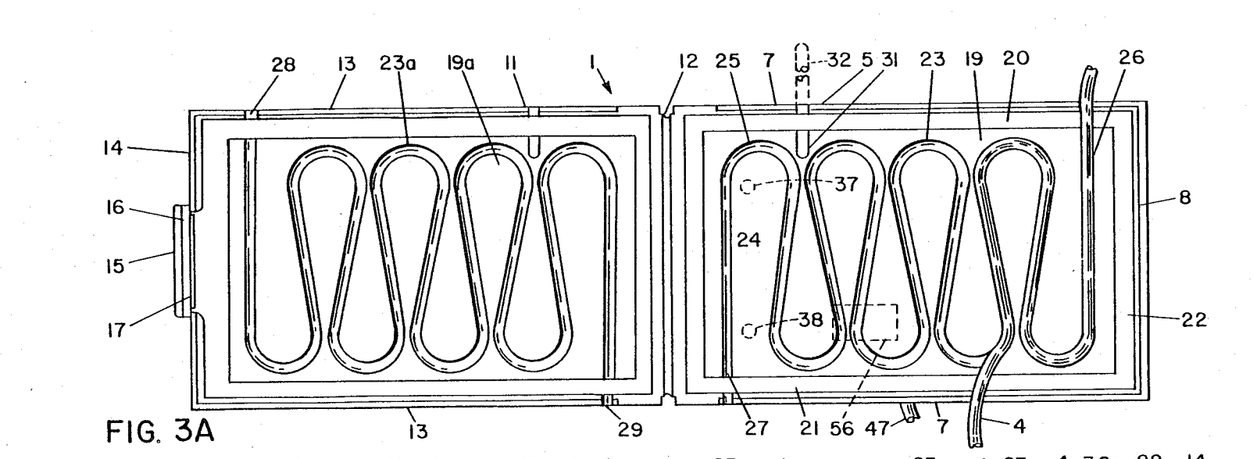
FIG. 3A is a top plan view of an alternate embodiment of the fluid warmer of the present invention utilizing upper and lower heated plates with a different sinuous-shaped groove configuration, shown with the hinged cover opened.
Figure 4A:
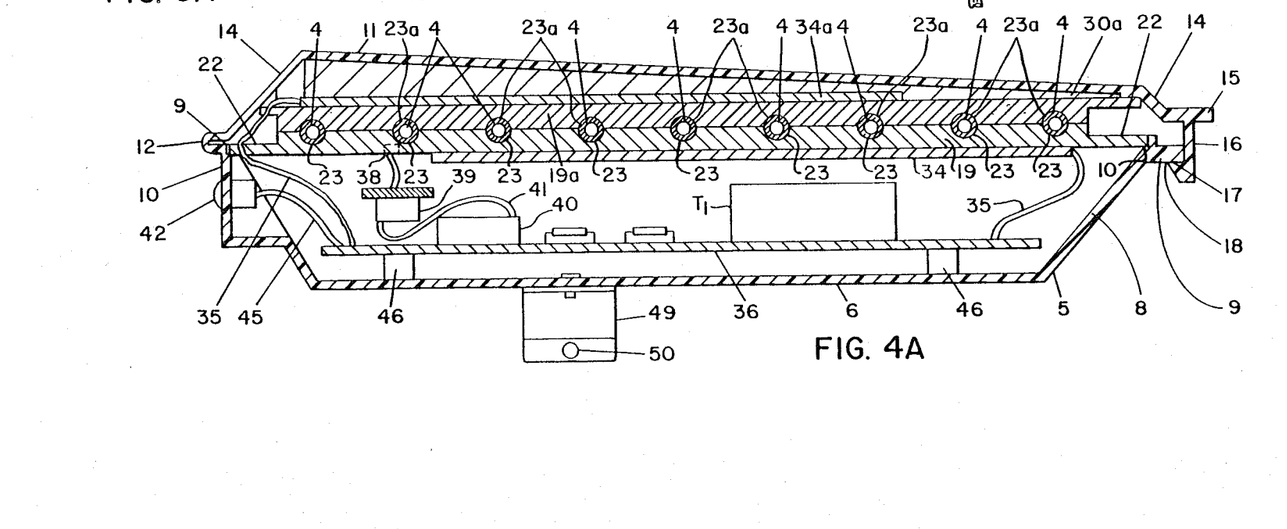
FIG. 4A is a cross sectional view of the fluid warmer illustrated in FIG. 3A taken along the longitudinal centerline of the warmer with the hinged cover in the closed position.

An alternate embodiment of the present invention is illustrated in FIG. 3A and FIG. 4A, where elements similar to those described hereinabove have been similarly designated. In this arrangement, the straight portions of the sinuously-shaped groove 23 are arranged in non-parallel relationship, thereby increasing the overall length of grooves 23 within blood warmer 1, while maintaining the same degree of curvature of the arcuate portions of the groove in order to avoid excessive bending or kinking of the supply conduit 4. This construction permits a greater length of supply conduit to be used in the blood warmer, and consequently, a greater degree of surface area of the fluid to be brought into contact with the heating means so as to provide faster and more uniform heating of the fluid. As noted hereinabove, as many convolutions of the groove may be provided as necessary in a particular application.

To further improve the heating efficiency of the unit, a second rectangular substantially planar heat conducting heating plate 19a, similar in construction to heating plate 19, may be secured within cover 11 as illustrated in FIG. 4A. Plate 19a may be constructed of any suitable heat conducting material such as anodized aluminum or the like. Plate 19a may be secured along its peripheral edge to cover 11 so that when the cover is raised, plate 19a moves with it.

The lower surface of plate 19a may be provided with a continuous sinuously-shaped groove 23a of a mirror image to groove 23 so that when plates 19 and 19a are placed together in abutting relationship, the adjacent grooves form a continuous channel of circular cross section which holds the conduit firmly in place to provide uniform heating of the entire conduit surface.

Heat is supplied to upper heating plate 19a by means of a thin sheet-like electrically operated heating pad 34a, similar in construction to heating pad 34, secured in heat transfer engagement with the upper side of heating plate 19a. Heating pad 34a may comprise a resistance heating element of the type formed by a plurality of Nichrome wires sandwiched between rubber or other resilient facing sheets. Electric current is supplied to heating pad 34a to electrical conductors 35a from electronic control circuitry described hereinafter located on circuit board 36 positioned in the lower portion of enclosure 5.

The space between the upper surface of heating element 34a and the under surface of the top portion of cover 11 may be left empty or filled with an insulating material 30a.

Figure 7:
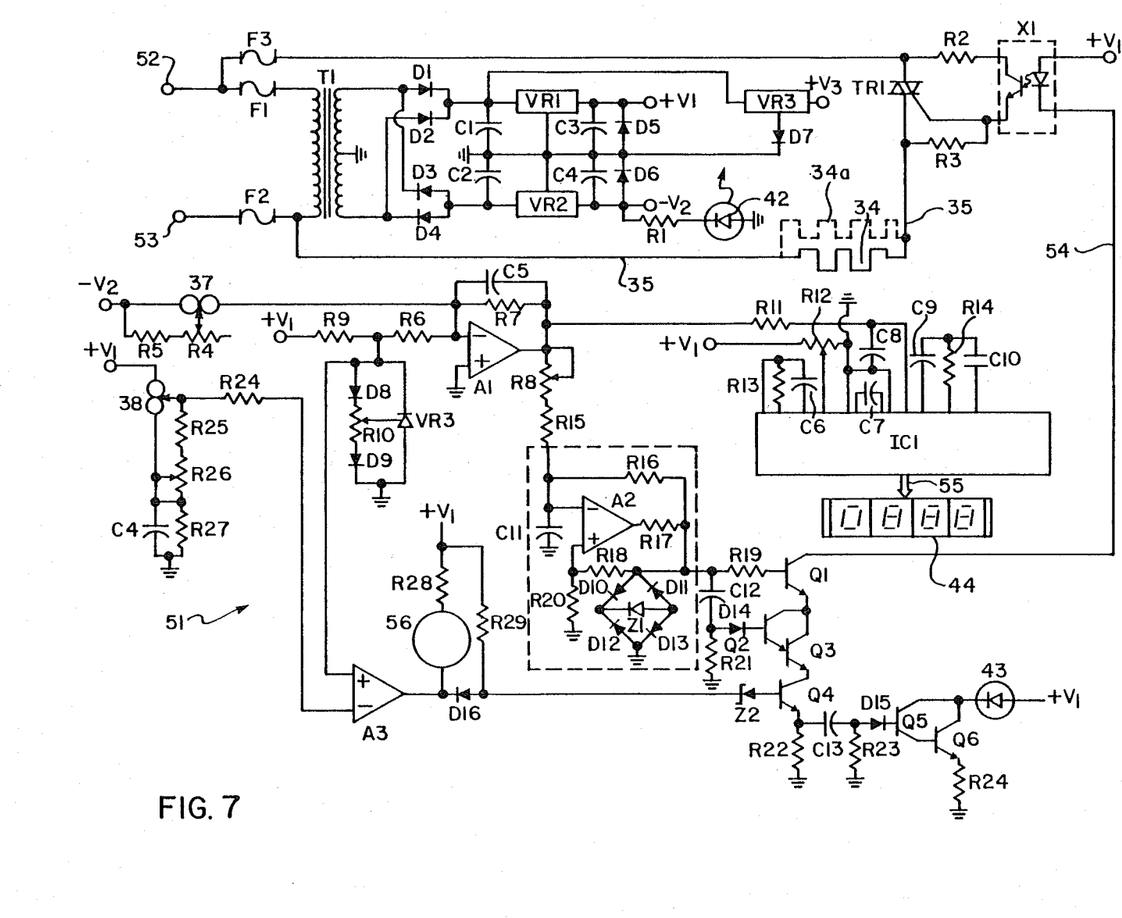
FIG. 7 is a schematic diagram of the electronic control circuitry of the present invention.

The electronic control circuitry of the present invention is illustrated generally at 51 in FIG. 7. Primary power is applied by power cord 47 to terminals 52 and 53, which supply transformer T1 primary through fuses F1 and F2, respectively. The center tap secondary of transformer T1 applies a full wave bridge rectifier formed by diodes D1–D4. The output from the rectifier is filtered by means of capacitors C1 C2, and regulated by voltage regulators VR1, VR2, and VR3, and associated components, to produce supply voltages $+V_1$, $-V_2$, and $+V_3$, respectively. Supply voltage $-V_2$ is supplied to the cathode of light emitting diode 42 to provide an indication when primary power is applied to fluid warmer 1.

Primary power is also supplied through fuse F3 to one terminal of triac TR1, and through resistor R2 to one terminal of the light receiving element of zero crossing optically isolated triac driver X1, which may be of the MOC 3030 type, manufactured by Motorola. The other terminal of the light receiving element is connected to the gate electrode of triac TR1, and through resistor R3 to the remaining terminal of the triac, which is also connected to one terminal of heating element 34. The remaining terminal of heating element 34 is connected through fuse F2 to neutral terminal 53.

The light emitting element of triac driver X1 is connected between supply voltage $+V_1$ and control line 54. It will thus be observed that when control line 54 is brought to a low level, the light emitting element of the triac driver X1 will be energized, turning on the light receiving element and consequently triac TR1, thereby causing current to flow through heating element 34, and heat to be supplied to heating plate 19. In the embodiment illustrated in FIG. 3A and FIG. 4A where a second heating element 34a is used in connection with a second heating plate 19a, the second heating element 34a may be electrically connected in parallel with heating element 34 as illustrated in FIG. 7. Consequently, current will flow through both heating elements to cause heat to be supplied to heating plate 19 and heating plate 19a simultaneously.

As described hereinabove, the temperature of heating plate 19 is monitored by means of a first temperature sensing element 37, and a second temperature sensing element 38. These temperature sensing elements, which may be of the LM334 type manufactured by National Semi-Conductor Corp., exhibit a current transfer which is proportional to the sensed temperature. The input of temperature sensing element 37 is connected through variable resistor R4 and fixed resistor R5 to supply voltage $-V_2$. The output of temperature sensing element 37 is connected to the inverting input of operational amplifier A1, as well as to the summing junction formed by resistor R6, resistor R7, and capacitor C5. The remaining terminals of capacitor C5 and resistor R7, as well as one terminal of variable resistor R8, are connected to the output of operational amplifier A1. The non-inverting input of the operational amplifier is grounded. The remaining terminal of resistor R6 is connected to the junction of resistor R9, the anode of diode D8, and the output terminal of voltage regulators VR3, which may be formed from a National Semi-Conductor LM336 voltage regulator unit. A variable resistor R10 is connected between the cathode of diode D8 and the anode of diode D9, while the cathode of diode D9 is connected to ground. The wiper terminal of variable resistor R10 is connected to the control input of voltage regulator VR3. The remaining terminal of resistor R9 is connected to supply voltage $+V_1$.

In the preferred embodiment illustrated, variable resistor R4 is adjusted until the voltage output of voltage regulator VR3 is 2.480 volts, which produces essentially a zero temperature coefficient voltage and allows a choice for resistor R6 which sets the current reference for zero degrees for the temperature sensor. Resistor R5 together with variable resistor R4 determines the proportionality constant for the temperature sensing circuitry. The specific components chosen in the present embodiment are such that the output voltage from operational amplifier A1 will be one tenth of the temperature in degrees centigrade monitored by temperature sensing element 37.

The output voltage from operational amplifier A1, which is representative of the temperature of heating plate 19 as monitored by temperature sensing element 37, is supplied through current limiting resistor R11 to the analog input of analog to digital converter IC1 which may be a 3½ digit digital panel meter chip such as Model No. ICL7106CPL manufactured by Intersil. The remaining components R12–R14 and C6–C10 associated with A/D converter IC1 serves as compensation and constant setting elements as is well understood in the art. The digital outputs from the analog to digital converter are supplied over output lines 55 to 3½ digit segment liquid crystal display 44. This arrangement serves to provide a visual numeric display of the actual temperature of heating plate 19. It will be understood by proper selection of the scaling components associated with IC1 and operational amplifier A1 that LCD display 44 may be caused by produce a numeric readout in any desired temperature units within the range of the display.

The remaining terminal of variable resistor R8 is connected through resistor R15 to the inverting input of operational amplifier A2, one terminal of resistor R16, and one terminal of capacitor C11. The remaining terminal of capacitor C11 is connected to ground, while the remaining terminal of resistor R16 is connected to the junction of resistor R17, R18, R19, C12, the anode of diode D10, and the cathode of diode D11. The remaining terminal of resistor R17 is connected to the output of operational amplifier A2, while the remaining terminal of resistor R18 is connected to the non-inverting input of operational amplifier A2 and to one terminal of resistor R20. The remaining terminal of resistor R20 is connected to ground. The cathode of diode D10 is connected to the cathode of zener diode Z1 and the cathode of diode D12, while the anode of diode D11 is connected to the anode of zener diode Z1 and the anode of diode D13. The anode of diode D12 and the cathode of diode D13 are connected to ground. It will be observed that the foregoing elements form a voltage controlled oscillator 101.

The remaining terminal of resistor R19 is connected to the base of transistor Q1. The collector of this transistor forms control line 54 for energizing heating element 34, while the emitter is connected to the collector of Darlington pair transistors Q2 and Q3. The base of the Darlington transistor pair is connected through diode D14 to the remaining terminal of capacitor C12, and through resistor R21 to ground. The emitter of the Darlington transistor pair formed by the emitter of transistor Q3 is connected to the collector of transistor Q4. The emitter of transistor Q4 is connected through resistor R22 to ground, and through capacitor C13 to the junction of resistor R22 and the anode of diode D15. The remaining terminal of resistor R22 is connected to ground while the cathode of diode D15 is connected to the base of a Darlington transistor pair formed by transistors Q5 and Q6. The collector of the Darlington pair is connected to the cathode of light emitting diode 43, while the emitter formed by the emitter of transistor Q6 is connected through resistor R23 to ground. The anode of light emitting diode 43 is connected to supply voltage $+V_1$.

In the operation of this portion of the electronic control circuit, the voltage output from operational amplifier A1 supplies the control voltage for the voltage controlled oscillator formed by operational amplifier A2 and associated components. Fundamentally, the specific values of resistors R16, R17, R18, R20 and C6 set the nominal frequency of oscillation. It will be observed that the output from operational amplifier A2 is clipped by the diode bridge consisting of diodes D10-D13. Consequently, current flow through resistors R8 and R15 perturb the nominal frequency of oscillation, as well as the percentage of time when the voltage output from operational amplifier A2 is a positive voltage. Variable resistor R8 is adjusted so that oscillation ceases when the temperature reaches a predetermined set point of 3.700 volts, corresponding to a nominal heating plate temperature of 37° C.

It will be observed that transistor Q1 is turned on whenever the output voltage from operational amplifier A2 is positive. In addition, as a result of the coupling through capacitor C12 and diode D14, the Darlington transistor pair formed by transistors Q2 and Q3 will be turned on only when an oscillating output is produced from operational amplifier A2. As will be explained in more detail hereinafter, transistor Q4 is normally turned on. Consequently, a conduction path for current flowing in control line 54 will exist through transistors Q1-Q4 only when the output potential from operational amplifier A2 is positive and oscillating. This action permits current flow in control line 54, thereby turning on optical isolator X1 and energizing heating element 34. It will be observed that component failure resulting in loss of oscillation or a negative output potential from operational amplifier A2 or both will cause immediate de-energization of heating element 34 to prevent over heating of the fluid in supply conduit 4, on the next zero crossing of the power line voltage.

It will be further observed that as long as an oscillating positive voltage exists at the emitter of transistors Q4, the Darlington pair formed by transistors Q5 and Q6 will also be turned on, thereby energizing light emitting dode 43 to provide a visual indication that the heating element is energized. In the event that component failure occurs as described hereinabove, or the fluid temperature exceeds the predetermined maximum temperature, light emitting diode 43 will become extinguished indicating that the heating element is de-energized.

The voltage reference formed at the output of voltage regulator VR3 is also applied to the non-inverting input of voltage comparator A3. In general, variable resistor R4 will be adjusted to set the level of this reference voltage at 2.480 volts as described hereinabove. The inverting input of comparator amplifier A3 is connected through resistor R24 to the input of temperature sensing element 38 and to one terminal of resistor R25. The remaining terminal of resistor R25 is connected through variable resistor R26 and the parallel combination of resistor R27 and capacitor C4 to ground. The wiper terminal of variable resistor R26 and the output terminal of temperature sensing element 38 are connected to the junction of capacitor C4 and resistor R27.

In general, variable resistor R26 will be adjusted to cause the output from comparator A3 to go to ground potential when the temperature measured at the heating plate by temperature sensing element 38 exceeds the reference voltage established at the non-inverting input of the comparator. When this occurs, the output of comparator A3 will become a ground level, energizing audible alarm 56 through series resistance R28. At the same time, current flow from supply voltage $V_1$ through resistance R29 and zener diode Z2 to the base of transistor Q4 will be interrupted by the cathode of diode D16 being brought to ground, thereby turning transistor Q4 off. With transistor Q4 off, current flow through control line 54 is interrupted thereby de-energizing heating element 34, while at the same time the oscillating voltage supplied through capacitor C13 is interrupted to extinguish light emitting diode 43, to provide a visual indication that the heating element had been de-energized. When the temperature of heating plate 19 as sensed by temperature sensing element 38 again falls below the predetermined maximum temperature, the output from comparator A3 will assume a high level, turning off alarm 56, and reverse biasing diode D16 to permit current flow from supply $V_1$ through resistor R29 into the base of transistor Q4 to re-establish current flow through heating element 34. Consequently, a second fail-safe feature is provided to prevent over-heating of the fluid in supply conduit 4. Together transistors $Q_1$, $Q_3$ and $Q_4$, with their related components, form switch control means 105 for controlling operation of triac TR1.

It will be understood that various changes in the details, materials, steps and arrangements of parts, which have been herein described and illustrated in order to explain the nature of the invention, may be made of those skilled in the art within the principle and scope of the invention as expressed in the appended claims. For example, while for purposes of an exemplary showing, the fluid warmer of the present invention has been described and illustrated as having a cover hinged along one transverse edge to provide access to the heating plate, it will be understood that the cover construction may be modified as required. For example, the cover may be hinged longitudinally so as to open from bottom to top, with a margin of the cover remaining attached to the fluid warmer. The number of straight portions 24 and arcuate portions 25 of groove 23 may be varied as required. The sensors, namely the LED and liquid crystal displays, may then be positioned on the fixed portion of the cover between the hinged portion and the edge of the unit to increase the visibility of the monitoring devices. It will be further understood that a plurality of the fluid warmer units may be used in cascade or series in case of emergency where fluid must be transferred at a very rapid rate. This arrangement provides warm parenteral fluid to the patient without loss of valuable time. In addition, in the embodiment of the invention illustrated in FIG. 3A and FIG. 4A where two heating elements are utilized, the temperature sensors may be used in conjunction with either or both of the heating plates 19 and 19a as desired.

The embodiments of the invention in which an exclusive property or privilege is claimed are as follows:

1. In an in-line warmer for heating parenteral fluid and the like supplied from a fluid container (2) through a flexible supply conduit (4) of the type having a box-like fluid warmer enclosure (5) including a closable cover (11), a substantially planar heating plate (19) positioned within the enclosure, one surface of the plate including a sinuously-shaped groove (23) configured to maintain a length of the supply conduit in heat transfer relationship with the plate for heating the fluid within the conduit, electric heating means (34) for heating the plate, and a semiconductor switch (TR1) operatively connected between said heating means and a source of alternating voltage (52) for controlling current flow to the heating means when said switch is activated, the improvement in combination therewith comprising means for maintaining the temperature of the plate at a predetermined temperature to prevent overheating of the parenteral fluid or the like comprising:

a first temperature sensor (37) attached in heat transfer relationship to said plate for providing a first electrical signal representative of the actual temperature of the plate;

a voltage controlled oscillator (101) responsive to said first electrical signal producing an oscillating output signal having a frequency of oscillation which varies with the temperature of the plate as sensed by said first sensor, said circuit being so designed that said oscillating output signal ceases whenever the temperature of said plate as sensed by said first sensor exceeds said predetermined temperature;

a second temperature sensor (38) attached in heat transfer relationship, to said plate for producing a second electrical signal representative of the actual temperature of the plate;

comparison means (A3) responsive to said second electrical signal for producing an output signal when the temperature of the plate as sensed by said second sensor exceeds a predetermined maximum permissible plate temperature value representative of the overheating temperature of the fluid; and switch control means (105) for activating said semiconductor switch to cause current flow to the heater means in proportion to the frequency of the oscillating output signal to heat the fluid only in response to the presence of said oscillating output signal and for deactivating the semiconductor switch to prevent current flow to the heater means in response to either the absence of the oscillating signal or to the presence of said comparison means output signal, or both, whereby component failure associated with said oscillator (101) or switch control means (105) will cause the oscillating output signal to cease, thereby de-energizing the heater means to prevent overheating of the fluid.

2. The fluid warmer according to claim 1 wherein said switch control means comprises first (Q1), second (Q3) and third (Q4) switch means operatively connected so that the semiconductor switch is activated to cause current flow to said heater means for heating the fluid only in response to the activation of all of said switch means, said semiconductor switch being deactivated to prevent heating the fluid in response to the deactivation of at least one of said switch means, said first switch means (Q1) being activated and deactivated in response to said oscillating output signal, means (C12) for AC coupling said oscillating output signal to said second switch means (Q2) so that said second switch is activated and deactivated in response to said oscillating output signal and the presence of said oscillating output signal, but is deactivated in response to the absence of said oscillating output signal to thereby prevent heating the fluid, said third switch means (Q4) being normally activated in the absence of said comparison means output signal and deactivated upon the occurrence of said comparison means output signal to thereby prevent heating the fluid.

3. The fluid warmer according to claim 1 including means (56) responsive to said comparison means output signal for providing a sensible indication when said maximum permissible plate temperature is reached.

4. The fluid warmer according to claim 1 including indicating means for providing a visually sensible indication of the temperature of said plate.

5. The fluid warmer according to claim 4 wherein said indicating means comprises numerical display means responsive to said first electrical signal positioned on the exterior of said fluid warmer for providing a direct numeric readout of the plate temperature.

6. The fluid warmer according to claim 1 wherein said predetermined temperature is about 37° C.

* * * * *